United States Patent [19]
Anderson et al.

[11] Patent Number: 5,286,363
[45] Date of Patent: Feb. 15, 1994

[54] DYNAMIC MICROCHAMBER FOR MEASURING FORMALDEHYDE EMISSIONS

[75] Inventors: William H. Anderson, Conyers, Ga.; Chris W. Huber, Orangeburg, S.C.

[73] Assignee: Georgia-Pacific Resins, Inc., Atlanta, Ga.

[21] Appl. No.: 599,426

[22] Filed: Oct. 18, 1990

[51] Int. Cl.$^5$ .......................................... G01N 27/416
[52] U.S. Cl. ................................... 204/409; 204/431; 204/432
[58] Field of Search ................ 204/409, 424, 431, 432

[56] References Cited

U.S. PATENT DOCUMENTS

| | | | |
|---|---|---|---|
| 3,540,849 | 11/1970 | Neti et al. | 436/128 |
| 3,711,251 | 1/1973 | Goodson et al. | 436/130 |
| 4,017,373 | 4/1973 | Shaw et al. | 204/432 |
| 4,348,886 | 12/1982 | Faith | 73/19.07 |
| 4,357,824 | 11/1982 | Foss et al. | 73/19.05 |
| 4,409,293 | 10/1983 | Williams | 428/524 |
| 4,501,628 | 2/1985 | McGuire et al. | 156/62.8 |
| 4,541,902 | 9/1985 | Kinoshita et al. | 204/153.16 |
| 4,542,640 | 9/1985 | Clifford | 73/31.06 |
| 4,569,826 | 2/1986 | Shiratori et al. | 422/90 |
| 4,670,405 | 6/1987 | Stetter et al. | 436/151 |
| 4,692,220 | 9/1987 | Auel et al. | 204/153.2 |
| 4,835,393 | 5/1989 | Krauss | 250/373 |
| 4,888,295 | 12/1989 | Zaromb et al. | 436/161 |

OTHER PUBLICATIONS

Christensen, R. L., et al., "Measuring Formaldehyde Emissions Using a Small Scale Chamber," Proceedings of 23rd International Particleboard/Composite Materials Symposium, Apr. 4–6, 1989, pp. 55–64.
Formaldehyde Analyzers, Interscan Corp. Brochure, undated.
Instruction Manual LD Series Analyzer Model 16 Formaldehyde.
Gylseth, B., "Formaldehyde Emissions from Panel Products—Requirements and Trends," To Be Presented at the 1989 Asian Methanol Conference, Oct. 30–Nov. 1 (partial copy).
Anderson, W. H., et al., "Formaldehyde Quality Control Testing of Wood Products Using a Small Dynamic Chamber," Abstracts, 24th International Particleboard/Composite Materials Symposium, Apr. 3, 1990.
Georgia-Pacific brochure "The Small Dynamic Chamber" (bearing a copyright date of 1990).
"Small Chamber"—G-P Martell Version.
Lehmann, W. F., "Correlations Between Various Formaldehyde Proceedings" 17th International Particleboard Symposium, Mar. 1981.
Silberstein, S., et al., JAPCA, 38:1403–1411 (1988), "Validation of Models for Predicting Formaldehyde Concentrations in Residences due to Pressed-Wood Products".
Hanetho, P., "Formaldehyde Emission from Particleboard and Other Building Materials: A Study from the Scandinavian Countries," Proceedings 12th Symposium on Particleboard, pp. 275–286 (1978).
Rybicky, J., Wood and Fiber Science, 17(1):29–35 (1985).
Methanol Chemie Nederland vof (hand dated 1982).
Formaldehyde Test Method-2, NPA/HPMA Formaldehyde Test Method-1, NPA/HPMA/FI.
Black, M. S., "Evaluation of Formaldehyde Surface Emission Monitor", Final Report Prepared for The Formaldehyde Institute Jan. 6, 1984.
Matthews, T. G., et al., JAPCA, 37:1320–1326 (1987), "Interlaboratory Comparison of Formaldehyde Emissions from Particleboard Underlayment in Small-Scale Environmental Chambers".
Myers, G. E., et al., Forest Products Journal, 31(7):39–44 (1981), "Emission of Formaldehyde by Particleboard: Effect of Ventilation Rate and Loading on Air-Contamination Levels".
Matrutzky, R., Wood Based Panels International, "Investigations on Comparability of Large Chamber Tests for Formaldehyde Emission from Wood Based Panels", pp. 10–14, Oct. 1990.

Primary Examiner—John Niebling
Assistant Examiner—William T. Leader
Attorney, Agent, or Firm—Banner, Birch, McKie & Beckett

[57] ABSTRACT

A method and apparatus for measuring the formaldehyde emission of composite wood products bonded with urea-formaldehyde adhesives employing the combination of a small sample chamber and an electrochemical sensor.

16 Claims, 5 Drawing Sheets

DYNAMIC MICROCHAMBER FOR MEASURING FORMALDEHYDE EMISSIONS

BACKGROUND OF THE INVENTION

1. Field of the Invention

The present invention relates to apparatus and method for measuring in a short period of time formaldehyde emissions from composite wood products bonded with urea-formaldehyde resin adhesives. The invention particularly relates to apparatus and method for monitoring formaldehyde emissions of small samples of a composite wood product that gives results equivalent to those obtained using the large chamber test method adopted in 24 C.F.R. 3280.208 as the industry standard for measuring formaldehyde emissions from composite wood products.

2. Description of Related Technology

Composite wood products made from urea-formaldehyde (UF) resin adhesives, such as particleboard or medium density fiberboard (MDF), find use in a variety of applications. In many of these applications, the wood products are used in areas of restricted or limited ventilation, such as in the construction of mobile homes. Since formaldehyde off-gassing or emission from UF resin bound composite wood products is a potential problem in such applications, standards, such as those promulgated by the United States Housing and Urban Development Agency at 24 C.F.R. 3280.208, have been established defining the permissible maximum level of formaldehyde emission from UF bonded composite wood products. Unless wood products made with a UF resin adhesive meet these emissions standards, they cannot be certified for use and sale in the regulated applications.

A variety of methods have been developed to measure formaldehyde emissions from the planar surfaces of such composite wood products. Basically, the formaldehyde testing methods (FTM) fall into two categories: full scale tests, which are designed to give results comparable to the environment encountered in actual use, and lab tests, ostensibly for quality control monitoring, designed to mimic the results obtained using the large scale test protocol. The first full scale method, the FTM-2 test, was developed by the Hardwood Plywood Manufacturers Association (HPMA) and the National Particleboard Association (NPA). This test has since been modified and adopted in 24 C.F.R. 3280.208 as the standard test for determining formaldehyde emissions from particleboard products such as underlayment, mobile home decking, industrial board and the like. See, "Large Scale Test Method for Determining Formaldehyde Emission from Wood Products - Large Chamber Method FTM-2 - 1985", National Particleboard Association et al., Nov. 11, 1985 which is herein incorporated by reference. Wood products which show excessive levels of formaldehyde emission under this test protocol cannot be certified for sale as part of the NPA and HPMA Grademark Program for particleboard and hardwood plywood.

The FTM-2 test uses a test chamber of at least 20 m$^3$ (at least 800 ft$^3$) into which a plurality of full-sized (48–60 inches in width) panels are placed spaced apart by about 6 inches. Air is moved through the chamber at a rate sufficient to assure good mass transfer (eddy diffusion mass transfer) from the entire surfaces of the panel samples. Make-up air also introduced into the chamber, at a rate relative to the test chamber volume, to achieve a constant gas hourly space velocity (GHSV) or rate of renewal (Q/V) as calculated by dividing the make-up air flow rate (Q) by the test chamber volume (V). Under the regulatory program different board products are tested at different product loading conditions.

The boards first are conditioned for 7 days at 75° F. (about 24° C.) and 50% relative humidity prior to testing. The samples then are placed into the test chamber and after 16–20 hours, the level of formaldehyde emission in an FTM-2 test system is presumed to have achieved steady state. The steady state level of formaldehyde emission is then determined by measuring the formaldehyde concentration ($C_S$) in the circulating air. Formaldehyde concentration in the chamber air is measured in the FTM-2 test by bubbling a known volume of the chamber air through an impinger containing an aqueous solution of 1% sodium bisulfite. The bisulfite solution is then analyzed using the chromotropic acid method and a spectrophotometer to determine its formaldehyde concentration. Using known techniques, the measured value is converted into a formaldehyde emission value for the tested boards and compared against the established standards.

Although the FTM-2 test provides an accurate indication of the formaldehyde emission characteristics of the tested panels under the test conditions, the FTM-2 method is not suitable for routine process quality monitoring in a manufacturing facility. Not only is the long test interval prohibitive for measuring $C_S$, including the week-long conditioning period and almost a full day for the test, but the FTM-2 test is also deficient as a method for assessing equilibrium formaldehyde emission ($C_{eq}$) and the mass transfer coefficient (K) for the composite wood products.

A laboratory test purportedly developed to provide data that correlates to the full-sized FTM-2 test has been named the FTM-1 test. The FTM-1 test (also known as "the desiccator test") is a faster test method, which after a 24 hour conditioning period, requires only about 2 hours before a result is obtained. See, "Small Scale Test Method for Determining Formaldehyde Emissions from Wood Products, Two Hour Dessicator Test FTM-1 - 1983", National Particleboard Association et al., October 10, 1983 which is herein incorporated by reference.

To conduct the FTM-1 test, a plurality of small samples are placed in a desiccator containing a petri dish with 25 ml of distilled water. After 2 hours a sample of the water (about 4 ml) is analyzed by the chromotropic acid method wherein the concentration of formaldehyde is measured by monitoring the color of the solution using a spectrophotometer.

The FTM-1 test, however, has a number of shortcomings. First, the test procedure relies on molecular diffusion from the test specimens into the solution rather than on the more efficient eddy mass transfer obtained under conditions prevailing in the large scale test chamber. Secondly, the FTM-1 measuring method places an aqueous solution in the same environment as a formaldehyde-emitting surface. It is well known that formaldehyde emission from a composite wood product is strongly influenced by the conditions of exposure, particularly the prevailing humidity. The aqueous solution necessarily affects the humidity in the desiccator and thus the rate of formaldehyde emission from the tested samples.

Finally, the nature of the test is such that the same test results are obtained even when the total surface area of the wood composite samples is changed, indicating that the desiccator does not respond in a way similar to the large scale test chamber. This results in part because the amount of formaldehyde that is absorbed by the test solution in the FTM-1 test disturbs the emission equilibrium of the composite wood product sample and thus affects the amount of formaldehyde emitted from the samples contained in the test chamber. In other words, the aqueous solution acts as a formaldehyde sink increasing formaldehyde emission from the test samples rather than simply serving as an impartial monitor of equilibrium formaldehyde concentration in the test chamber. See Kinectics for Desiccator Jar and Alike Tests for Formaldehyde Release from Particleboard, Rybicky, Jaroslav, Wood & Fiber Science, Vol. 17, No. 1, January 1985.

Because of these and other inadequacies in the FTM-1 procedure, attempts to correlate its emission tests results with results obtained using the large scale chamber (FTM-2), which as noted above serves as the regulatory standard, have been less than satisfactory. Consequently, saddled with such testing inadequacies, mills producing composite wood products have been forced to operate with a wide production margin to ensure that certified board products meeting the formaldehyde emission limits of the appropriate standards are consistently obtained. Moreover, because only a single measure of formaldehyde can be determined, the FTM-1 test is deficient as a quality control tool in the manufacturing environment even if consistent results are obtained. As noted above, a test procedure that also determine the mass transfer characteristics of the composite wood product is needed if it is to be useful for quality control. Therefore, it would be desirable to have an alternative test to the large scale FTM-2 procedure that would measure formaldehyde emissions quickly (e.g., in less than about 30 to 60 minutes), conveniently and inexpensively with good correlation to FTM-2 test results.

One might think that it would be an easy matter merely to scale down the FTM-2 test chamber while continuing to use the corresponding make-up air flow rate (GHSV or Q/V) and loading ratio, i.e., the ratio of sample area (A) to chamber volume (V) used in the FTM-2 protocol. In other words, using a smaller chamber designed for operation at the same constant Q/V with the same corresponding A/V to imitate the large scale chamber. Unfortunately, if the air sampling and monitoring protocol remains the same as in the FTM-2 test, i.e., a sampling flow rate of 1 liter/min. to ensure identical results, the minimum chamber size for the regulatory required Q/V of 0.5 would be 0.12 m$^3$ (about 4 ft$^3$), a not inconsequential size. The device would be smaller than the large scale test chamber but not yet useful as a quality control monitoring method because steady state conditions would still require 16-20 hours to achieve. Moreover, the reduced absolute air flow and emitted formaldehyde volume would have to be measured by some method. Through the impinger technique of the FTM-2 protocol could be used to measure steady state ($C_S$) formaldehyde emission from such a scaled down chamber, it can not be used to measure an equilibrium emission level because of formaldehyde mass balance and humidity problems also encountered with the FTM-1 method. Furthermore, the impinger technique for determining the steady state formaldehyde $C_S$ concentration itself requires a minimum of about 30 minutes to conduct to ensure an accurate determination of the formaldehyde emission level, and this is in addition to the time needed to reach steady state conditions.

It would be desirable to have a system for accurately measuring formaldehyde emission from composite wood products under both steady state and equilibrium conditions in less than about 30 to 60 minutes so that it could be correlated to the FTM-2 results and also serve as a useful quality control tool in the manufacturing environment.

SUMMARY OF THE INVENTION

It is an object of the invention to provide an apparatus, and a method for measuring steady-state formaldehyde emissions from composite wood products in a short time period of less than about 30 minutes.

It is another object of the invention to provide an apparatus, and a method for measuring equilibrium formaldehyde emissions from composite wood products in a short time period of less than about 60 minutes.

It is yet another object of the invention to provide a device useful for measuring for formaldehyde emissions from composite wood products having a test chamber with a volume of less than about 0.5 m$^3$ and preferably less than about 0.1 m$^3$.

In accordance with the objects noted above and others as will be recognized by those skilled in the art, the invention relates to an apparatus and a method for measuring formaldehyde emissions from composite wood products. The apparatus aspect of the present invention concerns an apparatus for measuring formaldehyde emissions from composite wood products bonded with a urea-formaldehyde resin adhesive, said apparatus comprising in combination:

a sample chamber having a volume of less than about 0.5 m$^3$ for holding at least one sample board of said composite wood product and permitting said board to emit formaldehyde in said chamber;

blower means for circulating air through said sample chamber and across said at least one sample board in said sample chamber; and an electrochemical formaldehyde sensor in fluid communication with the circulating air for rapidly measuring the concentration of formaldehyde in said air without consuming any significant amount of the emitted formaldehyde.

The measuring method using the apparatus described above comprises:

flowing air for less than about 30 minutes over at least one board sample of said composite wood product contained within a sample chamber to form a formaldehyde-containing air stream; and, passing a portion of said formaldehyde-containing air stream over an electrochemical formaldehyde sensor to measure the concentration of formaldehyde in said air stream, wherein said sensor does not consume any measurable amount of formaldehyde in said air stream.

The invention provides a practical means for monitoring formaldehyde emissions within a time frame required for effective manufacturing quality control.

DETAILED DESCRIPTION

Figure 1:
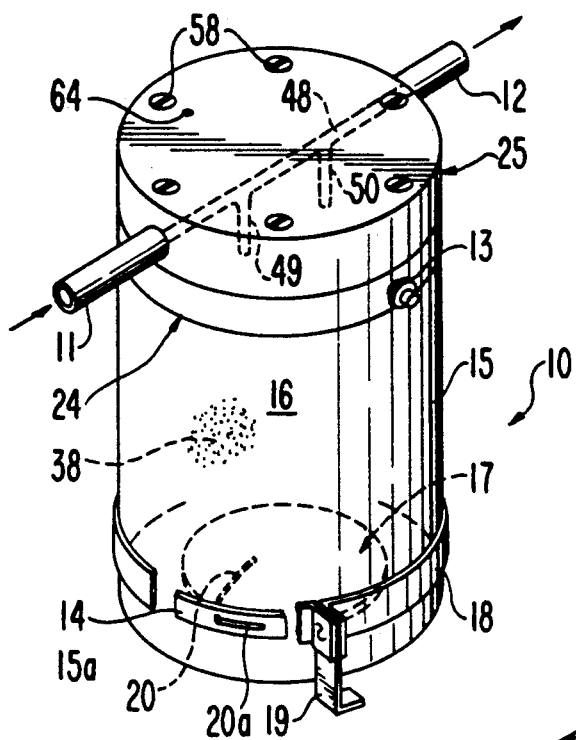
FIGS. 1 and 2 illustrate the construction of an electrochemical sensor that is useful in the present invention.

The present invention relates to apparatus and method for measuring formaldehyde emissions from composite wood board products that are bonded together with a high formaldehyde emitting adhesive, such as a urea-formaldehyde resin adhesive. Examples of such composite wood board products include, but are not limited to, hardwood plywood, particleboard, and medium density fiberboard (MDF).

The present invention capitalizes, in part, on the recognition that it is not necessary to maintain the same gas loading (Q/V) and the same sample loading (A/V) in a small sized chamber as that used in the large scale test chamber (FTM-2) in order to obtain statistically identical test results to the large scale chamber. Rather, as long as the ratio of the make-up air flow rate (Q) to the sample surface area (A) is held constant at the same value used in the large scale protocol and the chamber design accounts for adequate mass transfer, comparable results can be obtained. A recent article discussing calculations that support such conclusions is Christensen et al., "Measuring Formaldehyde Emissions Using a Small Scale Chamber", Proceedings 23rd International Particleboard/Composite Materials Symposium, Apr. 4–6, 1989 which is herein incorporated by reference. The present invention also is premised on the identification of a formaldehyde sensor that not only has a relatively rapid response time, but also consumes an insignificant amount of formaldehyde when performing the analysis.

Thus, the present invention provides a combination of a rapid response electrochemical formaldehyde sensor and an integrally connected, and specially designed small sample chamber. A key aspect of the present invention is that the apparatus can be used both to measure steady state formaldehyde emission values ($C_S$) for a composite board sample at a desired gas loading (Q/V) as well as to determine an equilibrium emission value ($C_{eq}$) for the sample, i.e., the formaldehyde emission in a closed system with no make-up air flow (Q/V=O). Most importantly, both of these determinations can be made in a very short time frame, on the order of minutes instead of hours as required by the large scale test chamber, and the measured values have a high statistical correlation to results which would be obtained on the same board samples using the testing protocol required by FTM-2.

An electrochemical formaldehyde sensor with a rapid response time, operating on the voltametric principle is one key element of the present invention. Such sensors are relatively inexpensive and, most importantly, can determine the formaldehyde content of a gas sample with such a sufficiently low (essentially undetectable) level of formaldehyde removal from the gas sample as to leave the formaldehyde concentration of the gas essentially undisturbed. Unlike prior formaldehyde measuring methods used in determining formaldehyde emission of composite wood products, which methods, if not done on a large scale, affect the gas phase equilibrium due to high gas sampling requirements, the electrochemical formaldehyde sensor used in the present invention, by needing only a very small (essentially undetectable) quantity of formaldehyde to assess gas phase concentration, effectively eliminates the requirement of a minimum test chamber size. The sensor also does not add any significant amount of water into the test chamber and thus avoids creating a measurement error due to a varying humidity condition in the test chamber. Consequently, such measurement technique makes possible a significant reduction in the size of a test chamber for measuring formaldehyde emissions of composite wood board products; yet retains the ability to obtain results which are statistically equivalent to those obtained using FTM-2.

In general, electrochemical sensors operate by passing gas molecules from a sample through a diffusion medium and adsorbing the gas molecules on an electrocatalytic sensing electrode maintained at a sensing potential appropriate for the electrode. On the electrode, the adsorbed gas molecules react and generate an electric current in proportion to their gas phase concentration. The sensed current can then be compared against a calibration curve and used to determine the subject gas concentration in the sample. or can be calibrated using a known standard and visually displayed on a suitable meter.

An electrochemical sensing cell is a device which generates an electrical current preferably only in the presence of the targeted compound, e.g., the pollutant being measured. The magnitude of this current is proportional to the pollutant concentration, which may be indicated by a meter connected to the output of an amplifier which amplifies the current from the sensing cell. An electrochemical sensing cell incorporates two electrodes, one called a sensing electrode and the other called a counterelectrode, immersed in an electrolyte. When the gas containing the targeted pollutant contacts the sensing electrode, reactions occur which cause a current to flow in a circuit comprising the counterelectrode, the electrolyte, the sensing electrode and an external lead connecting the sensing electrode back to the counterelectrode. The magnitude of this current is proportional to the pollutant concentration in the gas. By appropriate selection of counterelectrode and electrolyte materials, the sensing cell may be made selective to a particular gas species.

Depending on the species to be detected, either oxidation or reduction occurs at the sensing electrode, and the complementary reaction occurs at the counterelectrode. For example, to detect formaldehyde ($CH_2O$), oxidation occurs at the sensing electrode, which preferably comprises a noble metal such as gold. Electrochemical reduction occurs at the counterelectrode, which may comprise lead in an electrolyte of aqueous potassium hydroxide.

A preferred sensor construction uses an external voltage bias to maintain a constant potential on the sensing electrode relative to a nonpolarizable reference counterelectrode. The term "nonpolarizable" refers to a counterelectrode that can sustain a current flow without suffering a change in potential. Such nonpolarizable counterelectrodes avoid the need for a third electrode and a feedback circuit. Because the oxidation and reduction potential for formaldehyde is known or readily determinable by the exercise of no more than routine experimentation, the bias may be set to ensure that substantially only formaldehyde is reacted at the sensing electrode.

A particularly preferred formaldehyde sensor is commercially available from Interscan Corporation of Chatsworth, Calif. under the designation Intersean Model LD-16 and is described in U.S. Pat. No. 4,017,373. The general simplicity of the electrochemical sensors make them significantly less expensive than other direct measurement systems such as IR analyzers. The description of the Intersean patent is herein incorporated by reference but may be briefly described with reference to FIGS. 1 and 2 (from U.S. Pat. No. 4,017,373).

Electrochemical sensing cell 10 detects and measures the concentration of formaldehyde in a selective sample of circulating air from a sample chamber containing composite board samples. The withdrawn air sample containing emitted formaldehyde flows into the sensing cell 10 via conduit 11 and exits from tile cell via conduit 12. An appropriate pump knot shown) of either the positive pressure or suction type is used to force the contained air gas through sensing cell 10. It formaldehyde is present, a current will be generated between the sensing electrode terminal 13 and counterelectrode terminal 14. This current can be amplified and/or combined with other information concerning the sampled boards to drive a meter or other form of display means which indicates the formaldehyde concentration, for example, in parts per million.

Sensing cell 10 includes a cylindrical container 15, closed at the bottom 15a, that holds immobilized electrolyte 16 and a counterelectrode 17 immersed in the electrolyte. Metal clamp 18 surrounds the container 15 and serves the double function of mounting the sensing cell 10 to an L-bracket 19 and of providing electrical connection to the counterelectrode terminal 14. That terminal may comprise a thin strip of foil mounted on the outside of cylinder 15.

Wire 20 connected to the counterelectrode 17 extends through a hole in the cylinder 15 and has an end portion 20a that is bent back underneath the terminal strip 14. Clamp 18 covers the strip 14 and insures good electrical contact between the wire 20, the strip 14, and the clamp 18 itself.

Figure 2:
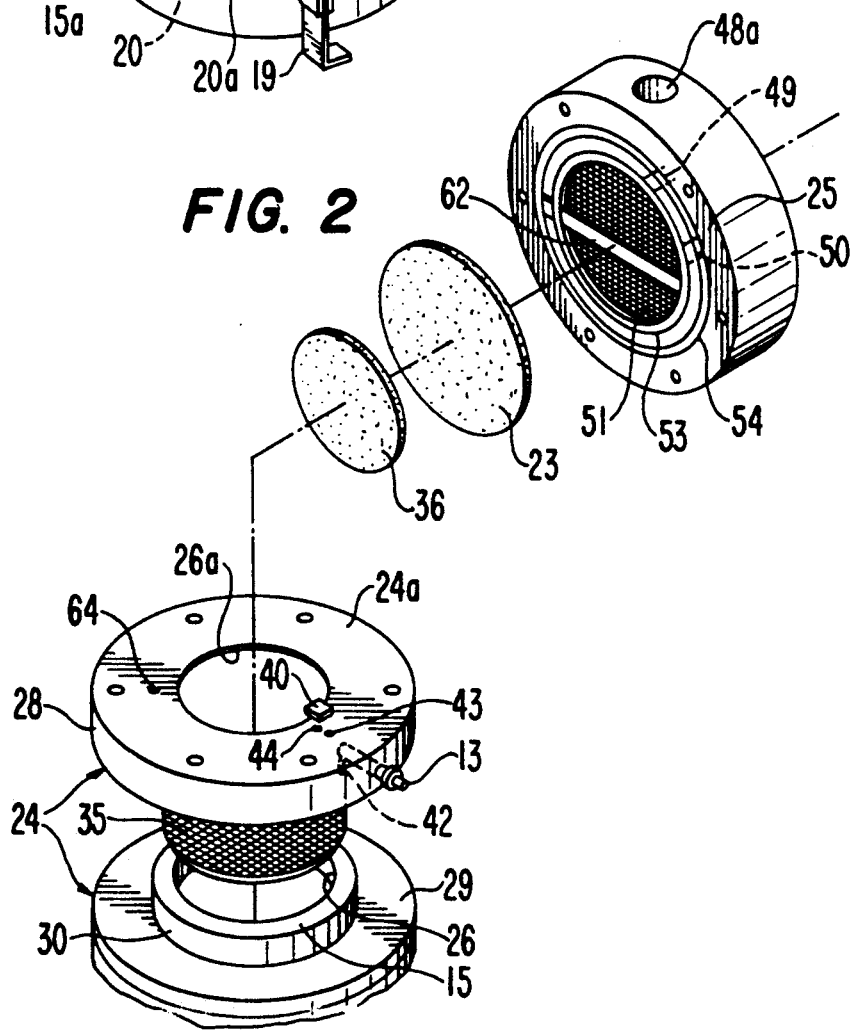

In FIG. 2, sensing electrode 23 is illustrated as planar. Sensing electrode 23 is clamped between a cover 24 that seats atop the open end 15b of the container 15 and manifold cap 25 to which the inlet and outlet conduits 11, 12 are connected. Cover 24 has a central opening 26 through which the electrolyte 16 can reach the sensing electrode 23. The lower surface 25a of the cap 25 includes a recess through which the gas to be analyzed reaches the sensing electrode 23. Voltametric sensing thus is facilitated, since the sensing electrode 23 is in contact with both cell electrolyte 16 via the opening 26 and the gas species supplied via the recess.

Screen 35 supports one or more discs 36 of filter material which function to ensure intimate contact between electrolyte 16 and the sensing electrode 23. To this end, screen 35 is formed of a material that is non-reactive with electrolyte 16 and which is sufficiently rigid to support the filter disc 36 without becoming concave at its center. Polyester is an appropriate material for screen 35.

Disc 36 has a diameter slightly less than the opening 26a so as to fit within this opening. Typically disc 36 comprises a glass filter paper such as that sold commercially. More than one such disc 36 may be required to fill completely the space between the screen 35 and the sensing electrode 23. The electrolyte flows through the screen 35 and completely wets the disc or discs 36. Since these are slightly compressed between the screen 36 and the sensing electrode 23, intimate contact is obtained between the electrolyte that saturates the disc or discs 36 and the sensing electrode 23.

To prevent sloshing of electrolyte 16 within the cell 10, container 15 may be filled with an inert, absorbent material 38, such as glass wool, to immobilize the electrolyte. The absence of free electrolyte eliminates undesirable sensor noise and is particularly advantageous when high amplifier gain is required for low concentration readings.

Only a small portion of the gas circulating through the sample chamber is needed and should be supplied to the sensing electrode 23. To this end, a through passageway 48 is provided in the cap 25 between the inlet conduit 11 and the outlet conduit 12. A pair of lateral ports 49, 50 branch off from the passageway 48 and extend to the recess in cap 25 mentioned above. Ports 49 and 50 are spaced apart so as to be adjacent the edges across the recess. With such placement, some of the gas entrant through the conduit 11 will flow through the branch port 49, into the recess and then out through the port 50 and the outlet conduit 12. Intimate contact between this sample gas and the counterelectrode 23 thus is accomplished within the recess.

Due to the very low (essentially undetectable) formaldehyde losses encountered with the operation of the electrochemical sensor used in the present invention, the sample chamber can be substantially smaller than previous devices yet still can be used to determine equilibrium formaldehyde emission without introducing any sampling error into the determination of $C_{eq}$. A smaller sample chamber in combination with a large emitting surface area (i.e., a high sample loading area by using multiple samples) can come to equilibrium quickly (e.g. in less than about 30 to 60 minutes) and also provide a practical means for monitoring steady state formaldehyde emission rates.

The high loading also increases the obtention rate of steady state conditions, so that the data needed to assess fully the mass transfer characteristics of a board sample can be gathered in a very short time period. The desired sample chamber size, in accordance with the present invention for most quality monitoring methods is less than about 0.5 m$^3$, and preferably is less than about 0.1 m$^3$. In order to obtain formaldehyde emission results which are representative of a full sized (e.g. 4'×8') sheet of the composite wood product, it is preferred that the sample chamber have a volume of at least about 0.02 m$^3$ and be configured to hold at least three board samples, from each sheet.

A particularly useful sample chamber has a volume of about 0.044 m$^3$. With such small chamber sizes, it is convenient to use board samples having a planar surface area of about 0.45 to about 0.65 m$^2$ although the specific board sample size chosen will depend on the actual chamber size used and the material being tested. With boards expected to have relatively low mass transfer coefficients, one could use slightly larger board samples than those used with boards having relatively high mass transfer coefficients to keep the time periods similarly short needed to reach steady state and equilibrium conditions. Because sample chamber 300 places the boards in a serpentine path, the chamber can easily accommodate a variety of sample sizes, merely by changing the length of the samples, although the same sample size should be used for any given test.

Figure 3:
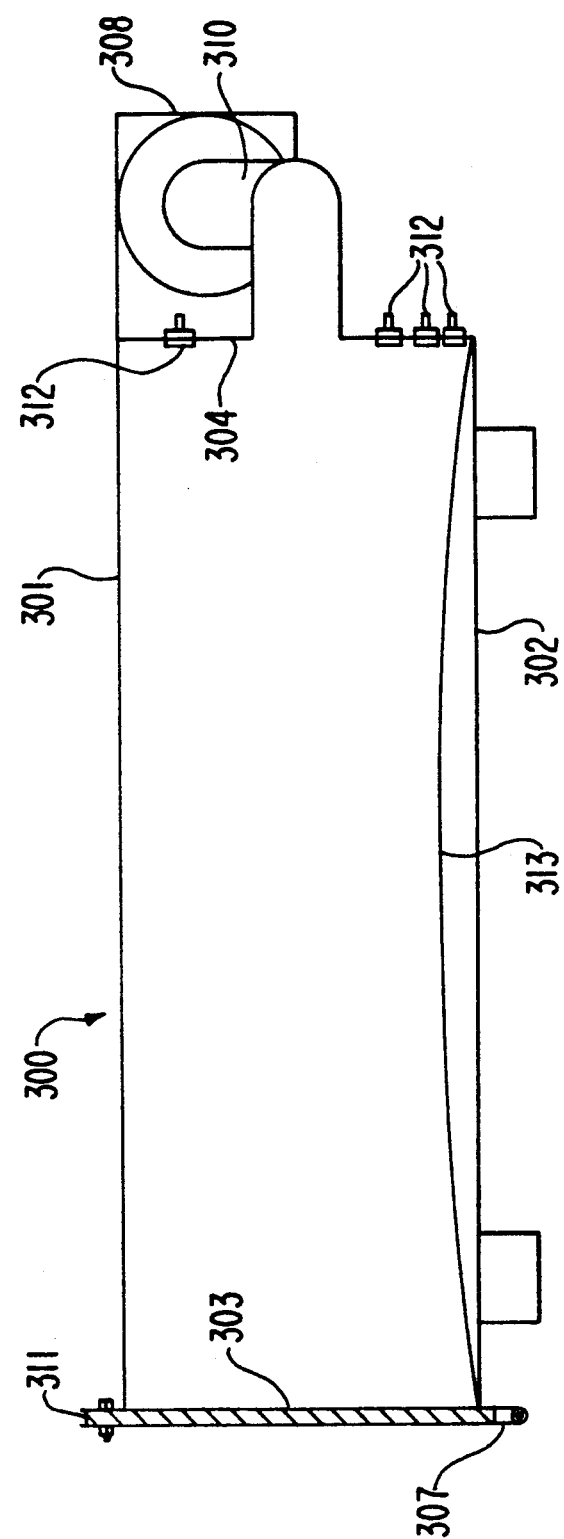
FIGS. 3 and 4 show side and top views respectively of a sample chamber useful in the invention.
Figure 4:
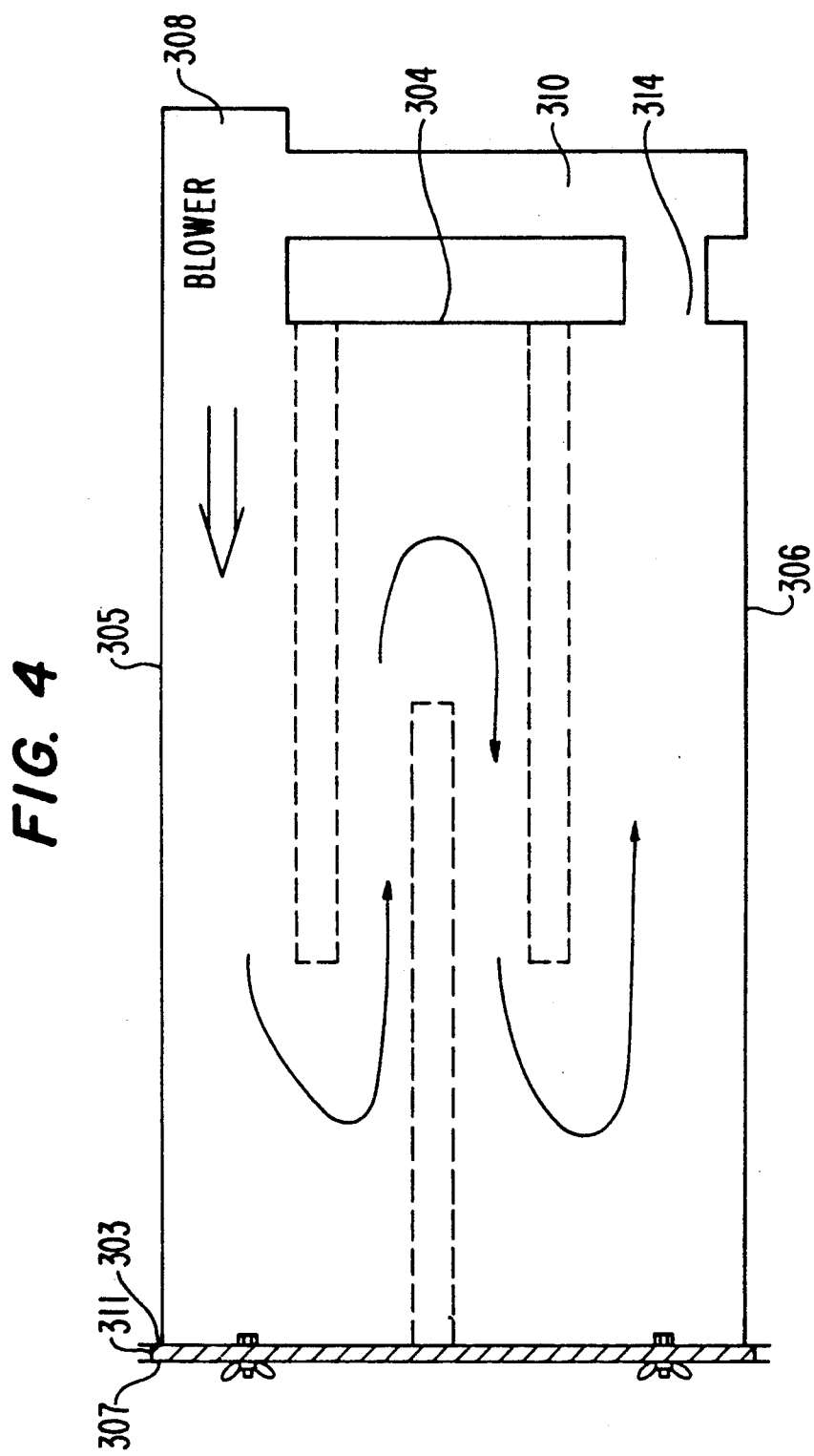

A side view of a particularly useful sample chamber is illustrated in FIG. 3 with a top view in FIG. 4 showing the placement of sample boards in the chamber. Similar structural features bear the same reference number in the various figures for convenience.

Sample chamber 300 is essentially a rectangular box having top wall 301, bottom wall 302, front wall 303, rear wall 304, and side walls 305 and 306. Hinged door 307 is located on front wall 303 and air blower 308 with recycle conduit 310 is located on rear wall 304. Suitable inside dimensions for chamber 300 are a width to about 13.8 inches (35 cm) a length of about 23.875 inches (60.6 cm) and height of about 8 inches (20.3 cm).

In combination with the arrangement of samples in chamber 300, blower 308 should be of a sufficient size to circulate the air within sample chamber 300 with sufficient velocity to ensure that eddy diffusion across the board sample surfaces is the principal mass transfer mechanism and to insure the absence of formaldehyde gradients within chamber 300. Typically, a blower capable of recirculating air at a flow rate of about 40 to 50 scan should be sufficient for the small chamber of the present invention.

Hinged door 307 is sealed to prevent gas leakage into or out of chamber 300 with any sealing means that is capable of maintaining an air tight seal around the perimeter of door 307. The illustrated sealing means is a closed cell foam 311 of the type commonly used for weather stripping around doors and windows and a pair of wing nuts. Other door sealing means including magnetic seals, hemispherical silicone strips, tongue-and-groove door construction details, and virtually any material useful for weather stripping are also suitable.

For sampling purposes, for inflow of make-up air, for exhaust and for bypass, sample chamber 300 includes a variety of ports 312 in rear wall 304 or side wall 306. Ports 312 are preferably positioned where air input or exhaust will not disrupt the air flow over the sample boards. The ports are designed so that they can be selectively used in conjunction with the operation of chamber 300.

In FIG. 4, chamber 300 holds three board samples vertically and the ports are located above the recycle conduit 310. The number of boards generally used is, to a certain extent, a matter of choice. Obviously, the chamber must contain at least one board. However, in order to provide the desired range of sample loadings in a conveniently sized sample chamber, applicants have found that the use of three board samples is suitable. Three boards reach steady state and equilibrium conditions much faster than a single board. Moreover, the use of three sample boards facilitates the realization of adequate mass transfer conditions in sample chamber 300. The boards are arranged so that air circulating over the boards follows a serpentine path between the outer face of the first board and side wall 305, between the first board and second board, between the second board and the third board, and finally between the outer face of the third board and side wall 306. The sampling ports are located on rear wall 304 above and below opening 314 for recycle conduit 310 and in the path between the outer face of the third board and right wall 306. Preferably the boards are evenly spaced in chamber 300 to provide a uniform flow condition in the chamber.

The edges of a board sample of a composite wood product, and particularly the edges of particleboard and MDF, generally have a much higher formaldehyde diffusion (emission) rate than the planar surfaces of the board. The edges also constitute a proportionately greater fraction of the total surface area of the board sample in the smaller sized samples used in connection with the present invention than in the full sized composite wood panels from which they come. Consequently, to obtain an accurate measurement of the formaldehyde emission of the board from which the samples were obtained, the edges of the samples should be sealed to prevent or retard formaldehyde emission during testing to avoid bias. Suitable sealing materials preferably include nonporous tapes and possibly non-volitile liquid sealants. A metal tape, such as aluminum tape, should be sufficient.

The boards should be positioned in chamber 300 in such a way as to prevent gas leaking and short circuiting directly from inlet to outlet. This is accomplished, for example, by sealing the boards against the top and bottom walls of chamber 300 to force the recirculating air to follow the desired serpentine flow path through chamber 300. The top and bottom edges of the sample boards may be considered as sealed if they are wedged between top 301 and bottom 302. Wedged fits are an efficient form of friction fit that unfortunately places unnecessary stress on sample chamber 300 and requires sample pieces that are accurately cut. An alternative friction fit can be accomplished more easily using a bent plate 313 disposed loosely inside chamber 300 over bottom wall 302. Preferably bent plate 313 is made of a material that does not absorb or react to formaldehyde and is able to withstand repeated flexure without permanent deformation. Particularly preferred materials include metals such as stainless spring steel.

Figure 5:
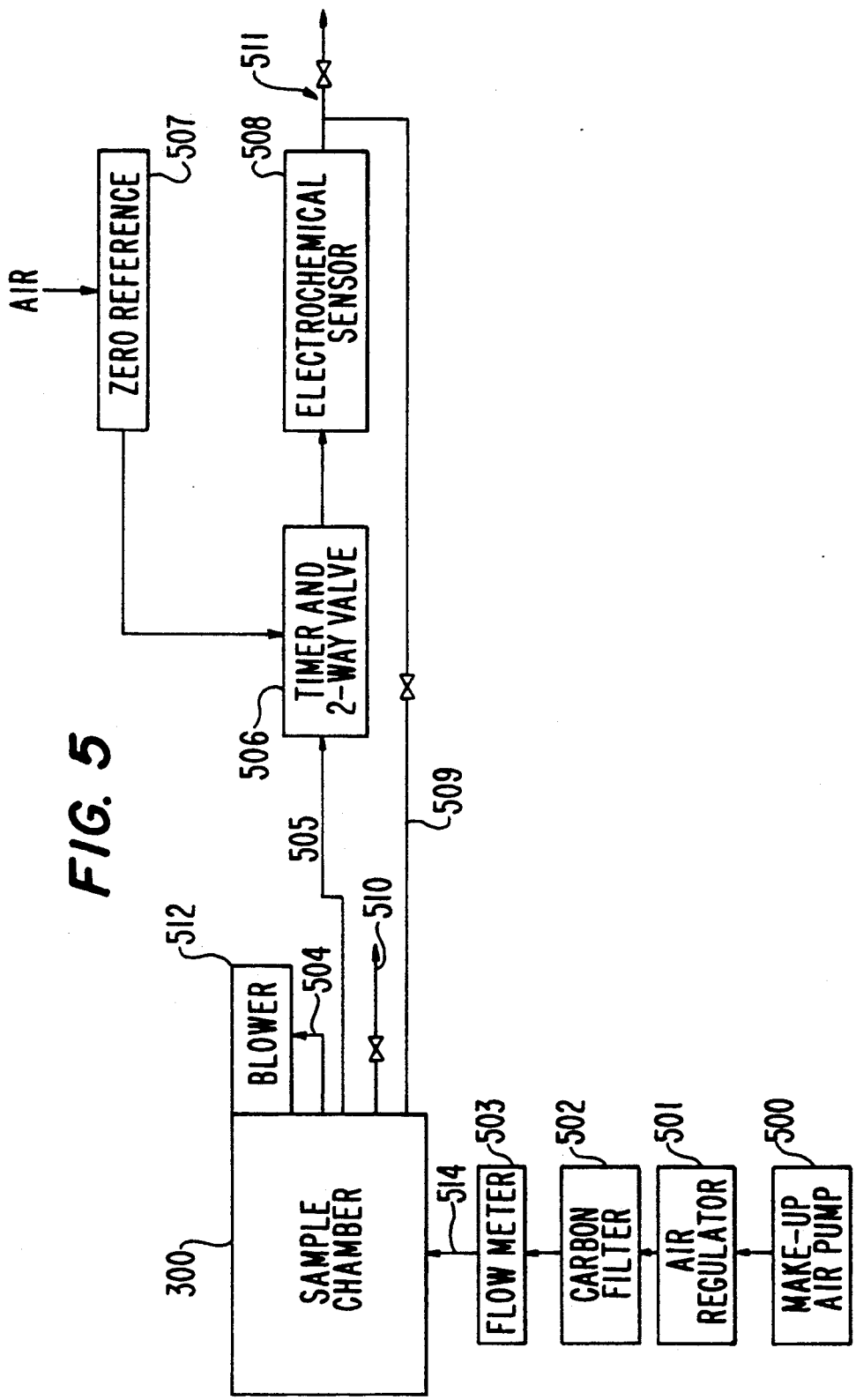
FIG. 5 is a block diagram of a sampling system.

FIG. 5 is a block diagram of the air flow arrangement for chamber 300 including the sample flow of a sensing system according to the invention. When measuring steady-state formaldehyde emissions ($C_S$), a make-up air pump 500 supplies ambient make-up air through an air regulator 501 and an activated carbon filter 502 via feed conduit 514 into chamber 300. The carbon filter is designed to remove contaminants, particularly ambient formaldehyde, that might interfere with proper measurement of formaldehyde emission levels in chamber 300. Flow meter 503 displays and allows control over the rate of make-up air introduced into sample chamber 300 through feed conduit 514. Any flow meter controller should be satisfactory for use in the present invention which permits accurate adjustment of the make-up air flow between 0 and that level needed to yield the appropriate ratio of make-up air flow to sample area (Q/A) equivalent to the regulatory testing protocol of FTM-2, i.e. 1.9 $m^3/m^2$-hr for MDF, 1.17 $m^3/m^2$-hr for particleboard and 0.53 $m^3/m^2$-hr for hardwood plywood. A suitable flowmeter is available from Cole-Parmer Instrument Co., Chicago, Ill. as model number N-03227-30. Make-up air is not used when measuring equilibrium formaldehyde emission values.

Blower 512 recirculates formaldehyde-containing air in sample chamber 300 via recycle conduit 504 so as to ensure adequate mixing within sample chamber 300. Sampling line or conduit 505 is used to remove a portion of the circulating air selectively during a sampling phase through timer and 2-way valve assembly 506 to the electrochemical sensor 508 containing an integral sample pump. Gas delivered to sensor 508 can be discharged through exhaust 511. Alternately, ambient air is flowed into the electrochemical sensor 508 through zero reference filter 507 and the 2-way valve 506 and is discharged through exhaust 511.

During operation of the sensor unit, gas, either ambient air or chamber air is constantly flowed through the formaldehyde sensor. Proper zeroing of the sensor output is done when filtered air is flowing through the senor. Recycle line 509, which is selectively connected to the exhaust line 511, such as by a valve, is used to route the circulated gas sample directly from electrochemical sensor 508 back to chamber 300. This arrangement would be used when measuring an equilibrium formaldehyde emission value.

Gas is exhausted from chamber 300 through valved exhaust port 510. The discharge ends of exhaust port 510, and exhaust port 511 of the formaldehyde sensor, are desirably positioned a sufficient distance from make-up air pumps so as not to introduce excessive ambient formaldehyde through filters 502 and 507. Preferably, the exhaust lines discharge into a room separate from the location of chamber 300 or outside.

A particularly useful feature of the present invention is that the above-described assembly can be operated in two modes. In a first mode, steady state formaldehyde emission values for a sample of a composite wood product can be determined at any desired make-up air loading. In its second mode, an equilibrium emission value for the sample boards can be measured. In both modes of operation, the samples are placed in chamber 300 and blower 308 is activated. When measuring a steady state emission, make-up air pump 500 also is activated and the flow meter is adjusted to provide the proper flow rate of make-up air through feed conduit 514 into chamber 300 to give the Q/A ratio appropriate for the composite wood product being tested. A portion of the recirculating air is exhausted through exhaust conduit 510 so as to maintain a proper mass balance. When a formaldehyde measurement of the recirculating air is taken by flow of a portion of the recirculating air through conduit 505, it is subsequently exhausted through exhaust conduit 511. Thus, in the steady state mode, recirculating air is discharged through port 510 and air flowed to sensor 508 is discharged through port 511. When an equilibrium emission in being measured, exhaust ports 510 and 511 are closed, make-up air flow into chamber 300 through feed conduit 514 is terminated and air flowed to sensor 508 through conduit 505 is returned to the sample chamber through recycle conduit 509. The system thus becomes close-ended.

Instead of having three separate valve-controlled conduits 509, 510 and 511, the system can be operated manually with only exhaust conduits 510 and 511, which in the equilibrium mode, are placed in flow communication to establish return line 509.

It has been observed that the electrochemical sensor used in the present invention has such reproducible response characteristics that it is not necessary, when measuring the formaldehyde emission of a board sample, to wait until the output of the sensor stabilizes. Rather, the sensor can be calibrated using a sample with a known formaldehyde concentration by tuning the output to the known value at any time after the initial response reaches about 80 to 90% of the known final output. This has been confirmed by calibrating the sensor to a known sample at various response times from 2 minutes to 20 minutes with no statistical difference in the subsequent results obtained. This is an important aspect of the method invention of the present application. Obviously, to minimize the test period, a shorter time for calibrating the sensor should be selected. In practice, calibration and testing at a 5 minute interval after the initial exposure has proved suitable in the preferred design.

Operation of the device for measuring formaldehyde emission starts with a calibration of the electrochemical sensor such as against a sample whose emission characteristics previously have been determined such as by using the large scale chamber or alternatively by using the small test chamber in combination with a conventional liquid absorption, i.e., impinger, test. In a preferred calibration technique, the known samples are inserted into chamber 300, blower 310 is activated and the make-up air flow rate appropriate for the composite wood product being analyzed is begun. During a time period sufficient for the known samples to reach steady state conditions, i.e. less than about 30 minutes and typically about 5 minutes, two-way valve 506 directs air from zero reference filter 507 into sensor 508.

Once a sufficient time has elapsed for the board samples having the known emission characteristics to reach steady state emission, the sensor is exposed to the formaldehyde source of the known concentration. This is done by setting the timer for the two-way valve for the appropriate exposure period, generally between 2 and 20 minutes with five minutes preferably being used. A portion of the gas from chamber 300 now flows through conduit 505 and into sensor 508. The flow rate of sampled gas should be adjusted to between about 0.3 to 0.7 liters per minute, typically about 0.5 liters per minute. If the flow rate to the sensor is too low, then the sensor response time is adversely affected and an accurate reading can not be obtained in the desired minimum time frame. Applicants have observed that if the flow rate is too high then the lifetime of the sensor is adversely affected. Also, too high a flow rate is undesired when measuring the equilibrium formaldehyde emission of a board sample. Under proper flow conditions, a sensor can be expected to last for about 300–600 hours of testing.

The instrumentally displayed sensor output then is tuned to the known formaldehyde emission value of the sample through span adjustment at the desired time after exposure of the sensor to the known formaldehyde source, typically about five minutes. All subsequent determinations of the steady state or equilibrium formaldehyde emission, i.e., concentration, of unknown board samples is then conducted at the same time interval after exposure as used for the initial calibration, e.g., about 5 minutes after exposure. Such calibrations are well within the existing skill for one in this art and are outlined in the protocol for the FTM-1 and FTM-2 tests.

In an alternative calibration technique, unknown board samples can be used. First, the above-described procedure is repeated three times to get an average emission value for the unknown sample at the existing setting. Then, the protocol is repeated again but instead of determining formaldehyde concentration using the electrochemical sensor, the exhaust from the small chamber is routed through a flow meter and into a liquid impinger for measuring formaldehyde by a wet chemistry technique. The previously measured values facilitate the wet chemistry analysis. According to the FTM-2 procedure, typically a thirty minute period for absorbing formaldehyde in the liquid impinger should be suitable. The samples then are rerun as above using the electrochemical sensor. The emission value obtained from the wet chemistry procedure then is used as the standard for adjusting the span on the sensor output upon rerunning the board samples a fourth time. Once calibrated, samples of unknown emission characteristics are loaded in the sample chamber and the air flow rates for the make-up air (if used) and sampling pump are adjusted as desired. Any number of sample boards can be used, but it is preferred to use a manageable number such as 3. An odd number of sample boards is preferred so that a serpentine flow around the boards can be preserved. For a sample size of 3 boards having the dimensions 7.875 inches × 15 inches, a sampling pump flow rate of 0.5 liters/min. in a sampling chamber of about 0.044 m³ (nominal ID of 24"×8"×14"), is suitable. Make-up air can be supplied at rates of up to about 15 liters/min. depending on the product being tested.

Prior to testing, board samples can be stored in hermetically sealed bags to arrest formaldehyde emission, and just prior to testing the samples are preferably conditioned for about an hour. The boards are conditioned under fixed conditions of temperature and ventilation. A conditioning temperature of 77° F. has proved suitable for producing results comparable with results obtained with FTM-2. The testing conditions are desirably about 75–79° F. and 46–54% relative humidity. The preferred testing conditions are 77° F. and 50% relative humidity.

Once the samples have reached steady state in test chamber, which requires less than about 30 minutes, e.g., the samples have been in the sample chamber with the appropriate flow rates for about 5–10 minutes, with air flow through the zero reference filter into the sensor, thereafter the time on the 2-way solenoid valve should be set to allow gas flow from chamber 300 and into the electrochemical sensor for about 5 minutes before returning to air flow through the zero reference filter. Readings are taken at intervals of 2, 4, and 5 minutes. At the end of the 5 minute interval, the 2-way valve will automatically return gas flow through the zero reference filter. The recorded emission value is the reading taken at 5 minutes. The reading sequence preferably should be repeated twice with different samples from the same board to ensure accuracy of the measurement.

The formaldehyde reading obtained should be corrected for 77° F. and 50% relative humidity. Such corrections are within the existing skill level for one in this art from the above mentioned protocol for the FTM-1 and FTM-2 methods.

As an example, if the reading at the end of 5 minutes is 0.25 ppm formaldehyde with a final temperature of 75° F. and a relative humidity of 54%, adjusting the reading for 77° F. according to the well known Berge et al. formula would add 0.03 ppm for the low temperature but subtract 0.02 ppm for the increased humidity. The corrected reading would be 0.26 ppm formaldehyde.

It is expected that the total testing assembly and method can be automated and through appropriate hardware and software integrated operated with computer assistance. The basic operations, however, remain as described above.

The readings from the dynamic microchamber of the invention show excellent correlation to readings from the FTM-2 large scale tests. The following is a list of actual readings obtained from both the FTM-2 test (which has an accuracy of 0.02 ppm) and the dynamic microchamber of the present invention.

| Dynamic Microchamber (ppm) | FTM-2 Large Chamber (ppm) |
| --- | --- |
| 0.135 | 0.13 |
| 0.31 | 0.32 |
| 0.12 | 0.13 |
| 0.21 | 0.21 |
| 0.17 | 0.18 |
| 0.184 | 0.18 |
| 0.138 | 0.14 |
| Correlation coefficient = 0.9907 | |

Example 2 - Medium Density Fiberboard

| Dynamic Microchamber (ppm) | FTM-2 Large Chamber (ppm) |
| --- | --- |
| 0.462 | 0.46 |
| 0.265 | 0.26 |
| 0.37 | 0.33 |
| 0.322 | 0.325 |
| 0.215 | 0.185 |
| Correlation coefficient = 0.9668 | |

As noted previously a particularly important aspect of the present invention is that the apparatus and method can be used for measuring, in a very short time frame both steady state ($C_S$) and equilibrium ($C_{eq}$) formaldehyde concentrations of a composite wood product. Consequently, the invention serves as a meaningful quality control tool for a manufacturing facility.

Figure 6:
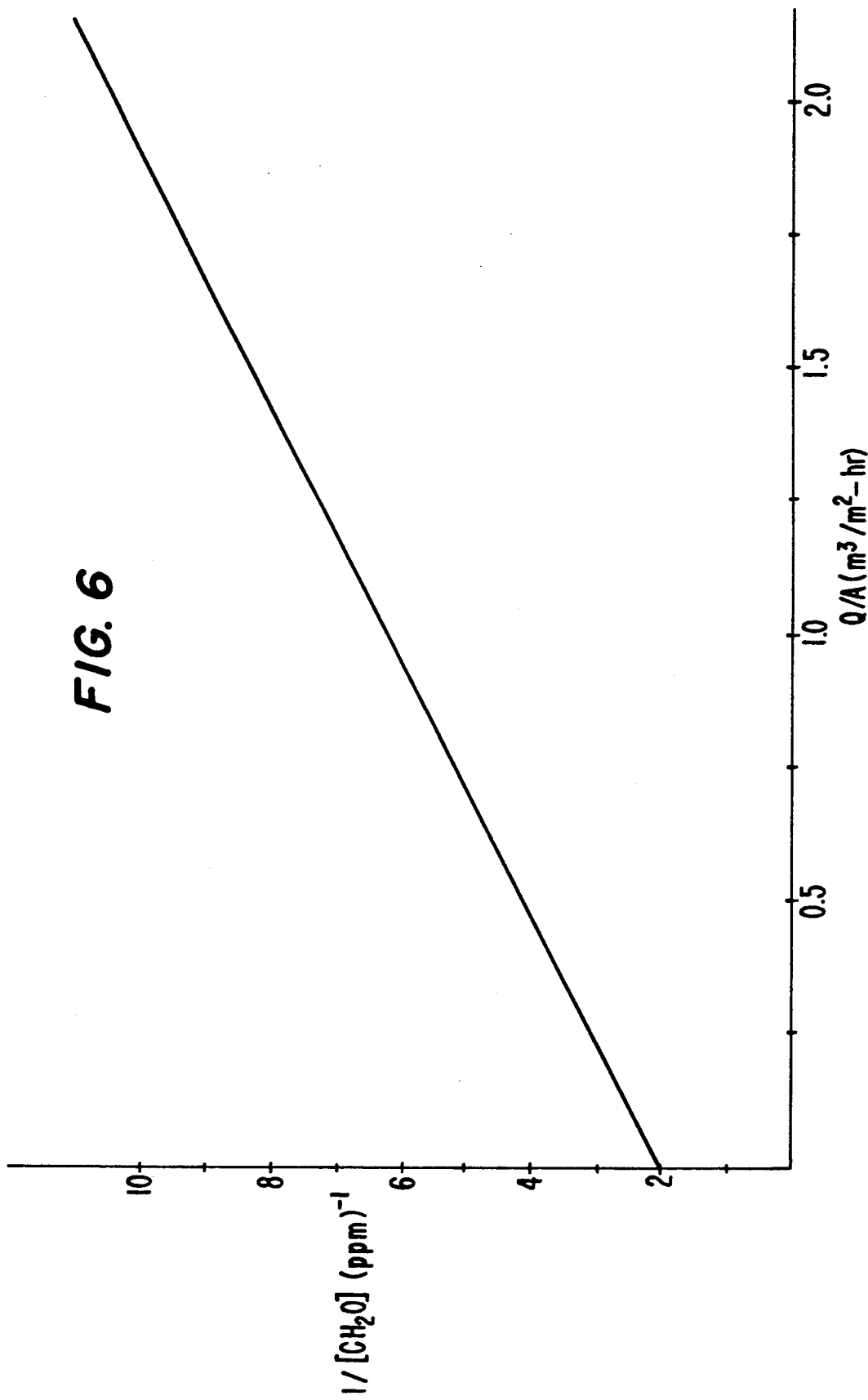
FIG. 6 is a graph showing the formaldehyde emission characteristic of a hypothetical sample of a composite wood product.

Formaldehyde emissions levels of composite wood products can be influenced by both changes in the UF adhesive chemistry and by process conditions during manufacturing, such as the relative application level of the adhesive and press conditions. Moreover, the emission characteristic of a given board can be considered as being based on two factors (1) the equilibrium emission characteristic of the board and the board's mass transfer coefficient (K). This is illustrated in connection with FIG. 6 which plots the reciprocal of formaldehyde concentration against gas loading (Q/A) for a hypothetical board sample. In the FIG. 6-type plot, the intersection of the line with the y-axis at Q/A=O is the reciprocal of the equilibrium emission concentration ($1/C_{eq}$), while the slope of the line times the "y" intercept is the mass transfer coefficient (K). Unless, one has available the information shown by FIG. 6 one has no way of knowing whether the level of emission is due to a high equilibrium emission level, generally a UF adhesive chemistry issue; or is due to a high mass transfer coefficient, generally a manufacturing issue. The present invention permits one to obtain the information needed to make this assessment in a very short time period. Thus, the invention constitutes a practical method for obtaining such data as an integral part of a mill's formaldehyde emission quality control program.

While certain specific embodiments of the present invention have been described with particularly herein, it will be recognized that various modifications thereof will occur to those skilled in the art and it is to be understood that such modifications and variations are to be included within the purview of this application and the spirit and scope of the appended claims.

We claim:

1. An apparatus for measuring formaldehyde emissions from composite wood products bonded with a urea-formaldehyde resin adhesive, said apparatus comprising in combination:

a sample chamber having a volume of less than about 0.5 m$^3$ for holding at least one sample board of said composite wood product and permitting said board to emit formaldehyde in said chamber;

blower means for circulating air through said sample chamber and across said at least one sample in said sample chamber;

a feed conduit for introducing ambient make-up air into said sample chamber, said feed conduit having a filter for removing contaminants from said make-up air;

an electrochemical formaldehyde sensor in fluid combination via a conduit with said air circulating in said sample chamber for measuring the formaldehyde concentration in said circulating air, wherein said electrochemical formaldehyde sensor can determine the formaldehyde content in said circulating air with a sufficiently low level of formaldehyde removal from said circulating gas as to leave the formaldehyde concentration essentially undisturbed in said circulating air during said measuring; and a recycle for returning air from said electrochemical formaldehyde sensor to said sample chamber.

2. An apparatus according to claim 1 wherein said sample chamber has a volume of less than about 0.1 m$^3$.

3. An apparatus according to claim 1 wherein said electrochemical formaldehyde sensor further comprises an electrocatalytic sensing electrode comprising a noble metal.

4. An apparatus according to claim 3 wherein said electrochemical formaldehyde sensor further comprises an immobilized electrolyte of aqueous potassium hydroxide.

5. The apparatus of claim 1 wherein a pumping means is connected to said feed conduit for pumping said make-up air into said chamber.

6. The apparatus of claim 1 having a valve and conduit for selectively flowing either filtered ambient make-up air or said circulating air in fluid communication with said electrochemical formaldehyde sensor.

7. An apparatus for measuring formaldehyde emissions from composite wood products bonded with a urea-formaldehyde resin adhesive, said apparatus comprising in combination:

a sample chamber having a volume of less than about 0.1 m$^3$ for holding at least three sample boards of said composite wood product, and permitting said sample boards to emit formaldehyde in said chamber;

blower means for circulating air through said sample chamber and across said sample boards in said sample chamber;

a feed conduit for introducing make-up air into said sample chamber, said feed conduit having a filter therein for removing contaminants from said make-up air;

a discharge conduit for discharging air from said sample chamber;

an electrochemical formaldehyde sensor in selective fluid communication via a conduit with the circulating air for measuring the concentration of formaldehyde in said circulating air, wherein said electrochemical formaldehyde sensor can determine the formaldehyde content in said circulating air with the sufficiently low level of formaldehyde removal from said circulating gas as to leave the formaldehyde concentration essentially undisturbed in said circulating air during said measuring; and a recycle conduit for returning air from said electrochemical formaldehyde sensor to said sample chamber.

8. The apparatus of claim 7 having a valve and conduit for selectively flowing either filtered make-up air or said circulating air in fluid communication with said electrochemical formaldehyde sensor.

9. An apparatus for measuring steady state formaldehyde emissions from composite wood products bonded with a urea-formaldehyde resin adhesive, said apparatus comprising in combination:

a sample chamber having a volume of between about 0.02 and 0.5 m$^3$ for holding at least one sample board of said composite wood product and permitting said board to emit formaldehyde in said chamber;

a feed conduit in flow communication with said sample chamber for introducing ambient air into said chamber, said feed conduit having a filter therein for removing contaminants from said ambient air;

blower means for circulating air through said sample chamber and across said at least one sample in said sample chamber;

an exhaust conduit for venting circulating air from said sample chamber;

an electrochemical formaldehyde sensor in selective fluid communication via a conduit with the circulating air for measuring the concentration of formaldehyde in said circulating air, wherein said electrochemical formaldehyde sensor can determine the formaldehyde content in said circulating air with a sufficiently low level of formaldehyde removal from said circulating gas as to leave the formaldehyde concentration essentially undisturbed in said circulating air during said measuring; and a recycle conduit for returning air from said electrochemical formaldehyde sensor to said sample chamber.

10. An apparatus according to claim 9 wherein said sample chamber has a volume of less than about 0.1 m$^3$.

11. An apparatus according to claim 9 wherein said electrochemical formaldehyde sensor further comprises an electrocatalytic sensing electrode comprising a noble metal.

12. An apparatus according to claim 11 wherein said electrochemical formaldehyde sensor further comprises an immobilized electrolyte of aqueous potassium hydroxide.

13. The apparatus of claim 9 wherein a pumping means is connected to said feed conduit for pumping said air into said chamber.

14. The apparatus of claim 9 having a valve and conduit for selectively flowing either filtered ambient air or said circulating air in fluid communication with said electrochemical formaldehyde sensor.

15. A apparatus for measuring steady state and equilibrium formaldehyde emissions from composite wood products bonded with a urea-formaldehyde resin adhesive, said apparatus comprising in combination:

a sample chamber having a volume of between about 0.002 and 0.1 m$^3$ for holding at least three sample boards of said composite wood product, and permitting said sample boards to emit formaldehyde in said chamber;

blower means for circulating air through said sample chamber and across said sample boards in said sample chamber;

a feed conduit for introducing ambient make-up air into said sample chamber, said feed conduit having a filter therein for removing contaminants from said make-up air, a first exhaust conduit for selectively discharging air from said sample chamber, an electrochemical formaldehyde sensor in selective fluid communication via a conduit with the circulating air for measuring the concentration of formaldehyde in said circulating air, wherein said electrochemical formaldehyde sensor can determine the formaldehyde content in said circulating air with a sufficiently low level of formaldehyde removal from said circulating air with a sufficiently low level of formaldehyde removal from said circulating gas as to leave the formaldehyde concentration essentially undisturbed in said circulating air during said measuring;

a second exhaust conduit for selectively discharging air from said electrochemical formaldehyde sensor, and a recycle conduit for selectively returning air from said electrochemical formaldehyde sensor to said sample chamber.

16. The apparatus of claim 15 having a valve and conduit for selectively flowing either filtered ambient make-up air or said circulating air in fluid communication with said electrochemical formaldehyde sensor.

* * * * *

UNITED STATES PATENT AND TRADEMARK OFFICE
CERTIFICATE OF CORRECTION

PATENT NO. : 5,286,363

DATED : February 15, 1994

INVENTOR(S) : William H. Anderson and Chris W. Huber

It is certified that error appears in the above-identified patent and that said Letters Patent is hereby corrected as shown below:

Column 15, line 66,

In claim 7, line 25 of the claim, "the sufficiently" should be --a sufficiently--.

Column 16, line 65,
In claim 15, line 6 of the claim, "0.002" should be --0.02--.

Columns 17 and 18, lines 16 and 1,
In claim 15, lines 25 to 26 of the claim, the phrase "with a sufficiently low level of formaldehyde removal from said circulating air" should be deleted.

Signed and Sealed this

Second Day of August, 1994

Attest:

BRUCE LEHMAN

Attesting Officer    Commissioner of Patents and Trademarks